(12) United States Patent
Oosting (10) Patent No.: US 7,813,476 B2
(45) Date of Patent: Oct. 12, 2010

(54) X-RAY BEAM PROCESSOR

(75) Inventor: Kenneth Oosting, Rocklin, CA (US)

(73) Assignee: Inspired Surgical Technologies, Inc., Roseville, CA (US)

(*) Notice: Subject to any disclaimer, the term of this patent is extended or adjusted under 35 U.S.C. 154(b) by 0 days.

(21) Appl. No.: 12/609,863

(22) Filed: Oct. 30, 2009

(65) Prior Publication Data
US 2010/0111246 A1   May 6, 2010

Related U.S. Application Data

(60) Provisional application No. 61/109,561, filed on Oct. 30, 2008.

(51) Int. Cl.
*G21K 1/06* (2006.01)

(52) U.S. Cl. .................... 378/85; 378/147

(58) Field of Classification Search ............ 378/84–85, 378/145–153
See application file for complete search history.

(56) References Cited

U.S. PATENT DOCUMENTS

| 7,321,126 B2 * | 1/2008 | Singer et al. ............ 250/492.2 |
| 7,542,548 B2 * | 6/2009 | Matsuo et al. ................ 378/84 |

\* cited by examiner

*Primary Examiner*—Hoon Song
(74) *Attorney, Agent, or Firm*—Jones Day (57) ABSTRACT

An x-ray beam processor and system that includes an x-ray beam generator for generating x-ray beams; a mirror shield for shielding the x-ray beams from select areas; a cylindrical waveguide for guiding x-ray beams traveling through the waveguide, which includes a plurality of entry ports and exit ports; a plurality of ring-shaped mirrors disposed adjacent to and generally parallel with the entry ports and the exit ports and sharing a common axis "X" with the waveguide; and mountings for mounting the mirrors to the waveguide.

14 Claims, 10 Drawing Sheets

Fig.10

X-RAY BEAM PROCESSOR

CROSS-REFERENCE TO RELATED APPLICATIONS

This application claims priority to provisional application No. 61/109,561, which was filed in the U.S. Patent and Trademark Office ("USPTO") on Oct. 30, 2008 and is incorporated herein by reference.

THE NAMES OF THE PARTIES TO A JOINT RESEARCH AGREEMENT

There has been no joint research agreements entered into with any third parties.

STATEMENT REGARDING FEDERALLY SPONSORED RESEARCH OR DEVELOPMENT

The federal government is not sponsoring any research or development related to the subject matter of this patent application.

BACKGROUND OF THE EMBODIMENTS OF THE PRESENT INVENTION

Cancer treatment systems that use an MRI device and a beam generator are known in the art. A number of existing treatment systems damage healthy tissue surrounding the cancerous tissue being treated. The beam processor and related systems described herein improve existing cancer treatment systems by, among other things, minimizing damage to the healthy tissue in the area surrounding the cancerous tissue being treated and provides greater assurance that the target tissue is killed. Such a system is disclosed in pending U.S. patent application Ser. No. 12/242,577 ("the '577 patent application"), filed on Sep. 30, 2008, and directed to a "Photonic Based Non-Invasive Surgery System That Includes Automated Cell Control and Eradication Via Pre-Calculated Feed-Forward Control Plus Image Feedback Control For Targeted Energy Delivery"; the contents of the '577 patent application are incorporated herein by reference and include a common inventor in Mr. Oosting.

A beam generator used in such a non-invasive system can include any source of x-ray beams such as linear accelerators and x-ray tubes. A problem with using x-ray beams is that they are not easily focused, and x-ray sources produce diverging x-ray beams that spread with the square of the distance from the source beam generator. Therefore, there is a need for beam processors that focus highly coherent and collimated x-ray beams on cancerous target cells with sufficient flux to destroy the cancerous cells.

BRIEF SUMMARY OF THE EMBODIMENTS OF THE PRESENT INVENTION

An embodiment of the present invention is directed to an x-ray beam processor system that includes an x-ray beam generator for generating x-ray beams; a mirror shield member for shielding the x-ray beams from select areas; a cylindrical or a system of conical waveguides for guiding x-ray beams traveling through the waveguide, which includes a plurality of entry ports and exit ports; a plurality of ring-shaped mirrors disposed adjacent to and generally parallel with the entry ports and the exit ports, and sharing a common axis "X" with the waveguide; and mountings for mounting the mirrors to the waveguide. In this embodiment, the mirrors are piezoelectric actuated to control their movement.

Another embodiment of the present invention is directed to an x-ray beam processor system that includes an x-ray beam generator for generating x-ray beams; a mirror shield member for shielding the x-ray beams from select areas; a cylindrical waveguide for guiding x-ray beams traveling through the waveguide, which includes a plurality of entry ports and exit ports; a plurality of ring-shaped circuit boards disposed adjacent to and generally parallel with the entry ports and the exit ports, where the circuit boards include a plurality of electrical chips; a plurality of polycapillary tubes with channels connected to the electrical chips; and a plurality of mountings for mounting the circuit boards to the waveguide. In this embodiment, the polycapillary tubes are actuated to control their movement.

Other embodiments of the present invention include features related to a beam processor with converging waveguides, double cone optics, inner cone optics, outer cone optics and outer cone optics with polycapillary tubes, as described in more detail below.

BRIEF DESCRIPTION OF THE DRAWINGS IN THE PRESENT INVENTION

DETAILED DESCRIPTION OF THE EMBODIMENTS OF THE PRESENT INVENTION

Figures 1A, 1B:
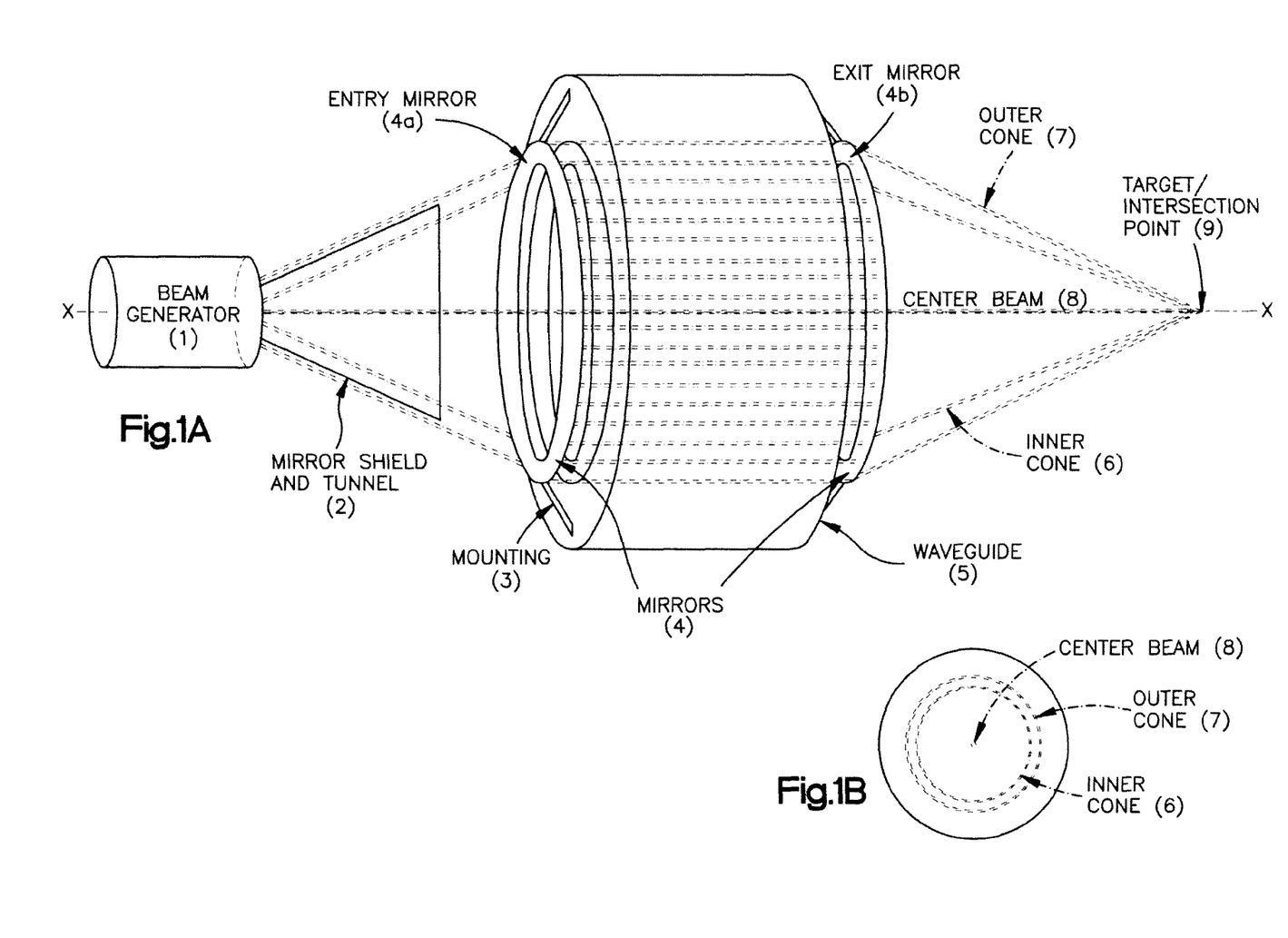
FIG. 1A is a side view of a first embodiment of the present invention showing the components in a beam processor.
FIG. 1B is a view from the target looking into the waveguide showing the inner cone, outer cone and center beam.

FIG. 1A shows a side view of a first embodiment of the present invention showing the components in a beam processor. The components of the beam processor according to the first embodiment include a beam generator 1, mirror shield and tunnel 2, mountings 3, mirrors 4 including entry mirrors 4a and exit mirrors 4b, waveguide 5, inner cone 6, outer cone 7, center beam 8 and target 9.

The beam generator 1 can include any source of x-ray photons but preferably the beam generator 1 includes linear accelerators, x-ray tubes or radioactive isotopes.

The mirror shield and tunnel 2 is preferably a precision machined lead (or other dense material) shield that prevents unwanted photons from reaching the mirrors 4.

The mountings 3 are preferably fixed structural components used to hold other components in fixed or near fixed position relative to one another. In the case of mountings for the actuated mirrors 4, the base of the mirror 4 is fixed to the mounting 3 while the mirror 4 is actuated (moved) relative to the base.

The mirror system includes multiple mirrors 4 with groupings of mirrors 4 (as shown on FIG. 2) for each port in the waveguide 5 except the center port. A set of one or more mirrors 4 will preferably be used at each end of each waveguide 5 except the center port. For example, for a beam processor with 513 ports, 1,024 sets of mirrors would preferably be used in the mirror system. The mirrors 4 will be described further below in relation to FIG. 2.

The waveguide 5 is preferably made of lead or other dense material such that the only photons reaching the opposite side from the beam generators 1 will be those photons passing through the waveguide ports. Thus, anything on the far side of the waveguide 5 is shielded from photons not directed into the ports. The waveguide 5 will have multiple ports or holes that permit directed photons to pass through such that each port functions as a wave guide. In one embodiment of the present invention, the individual ports are plated with gold such that the walls function as x-ray mirrors. The waveguides serve to provide collimation and a high level of coherence.

The waveguides are organized in three sets. There is an outer ring, an inner ring and a single center port. The photons form inner 6 and outer 7 cones as they travel from the exit ports of the waveguide 5 to the intersection point 9. Photons traveling from the beam generator 1 through the center port and on to the intersection point form the center beam 8. The target 9 is formed when the exit mirrors 4b direct the individual beams from each waveguide 5 exit port to come to an intersection at the desired target 9.

Figure 2:
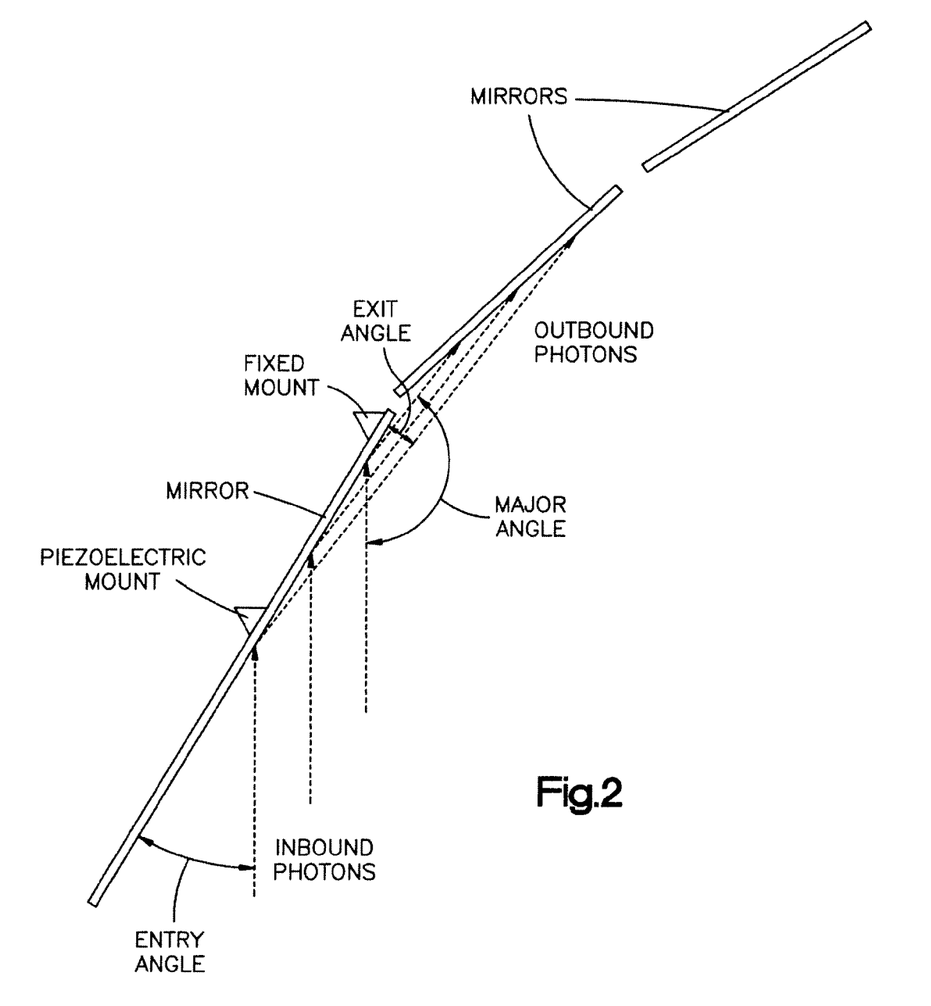
FIG. 2 is a view of an optic system used in an embodiment of the present invention showing mirror geometry and angles related to the actuation of the mirrors.

FIG. 2 shows a mirror's geometry and actuation as used in the mirror system 4 shown in FIG. 1A. More specifically, each mirror 4 is mounted on a fixed pivot point on one end and an actuator, preferably a piezoelectric actuator, at the other end so the deflection angle can be adjusted in very small increments. Any adjustment in a mirror 4 will affect deflections in subsequent mirrors and will likely require actuation (movement) of the subsequent mirrors. In the mirror's geometry and actuation for a given wavelength, the mirror's critical angle must not exceed 0.58 degrees therefore the entry angle as shown in FIG. 2 will preferably be approximately 0.50 degrees. In addition, the exit angle is approximately equal to the entry angle. Therefore, the total deflection at each mirror is approximately 1 degree and the major angle is approximately 179 degrees.

Figure 3:
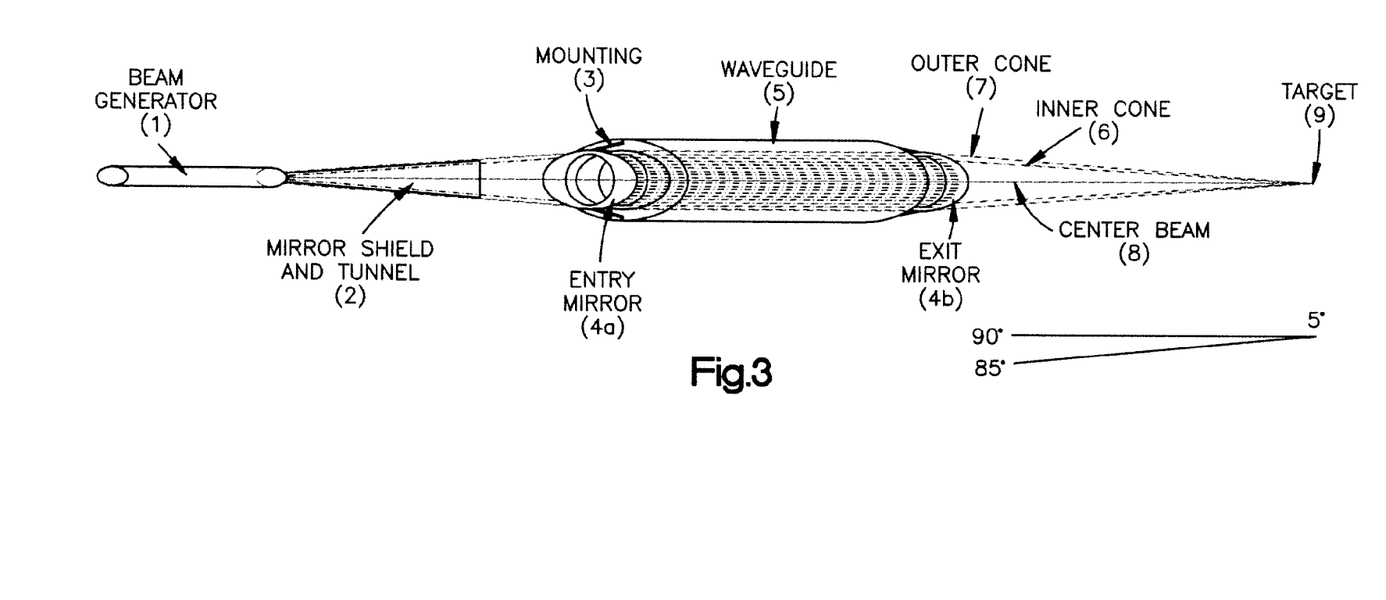
FIG. 3 is a top view of an embodiment of the present invention showing the various components of the optic system used in such an embodiment.

For example, as shown in FIG. 3, in a case where there are 5 mirrors in each segment of the rings there would be 5 degrees (or less than 10 times the critical angle for a given wavelength) of deflection, from 90 degrees to 85 degrees. If this is the case on both mirror rings and the wave guide is 36 inches long and the outer ring of ports is 4 inches in diameter, the total length from the beam generator 1 to the target 9 is approximately 7 feet.

If, however, a single mirror is used in each segment of the exit ring, the overall length increases to 22.86+36+114.58=173.44 inches or 14.45 feet (if a person of ordinary skill in the art draws a right triangle from the center of the outer cone 7 to the intersection point 9, the end of the triangle will be 2 inches and the angle at the intersection will be 5 degrees. Therefore, the length of the intersection point 9 from the waveguide 5 is 2/tan(5)=22.86. If you have only 1 mirror than the length=2/tan(1)=114.58 because the angle is only 1 degree.). This geometry would be required to feed the intersection point into a subsequent waveguide 5 with mirrored interior walls. The final output would approximate an x-ray laser. While photon density per unit volume would be hundreds of times greater at the output than the input, the brilliance would not likely be sufficient to qualify as an actual laser.

If these assemblies were then combined in a cascading arrangement of waveguides 5 and exit mirrors 4b, starting with multiple beam generators, the end result would be a brighter and brighter output as the number of inputs is increased.

While the beam processor provides a much higher concentration of photons at the intersection point 9 than would be available in the same size volume element of an unmodified cone beam or intensity-modulated radiation therapy ("IMRT") beams, the overwhelming majority of the energy emitted from the beam generator 1 to the beam processors will be discarded. This is because only the energy captured by mirrors 4 and channeled into the waveguides 5 is used. This selective use of photon streams dramatically reduces the total energy introduced into the patient and therefore reduces the likelihood of undesirable side effects while assuring ample treatment of the target cells.

The percentage of the input beam that is put to use can be varied between 0% and 0.0001% (approximately and depending on the number of beam mirrors/channels/photon streams).

The actuators on each mirror 4 can be used to modulate each photon stream on and off. By modulating a portion of the mirrors 4 to direct their photon stream such that it does not enter the corresponding waveguide 5 the beam intensity can be modulated up and down very rapidly. This modulation can be used to create the lower power beams for aiming as well as the energy burst for target cell destruction.

All unused portions of the input beam are preferably shielded to prevent unnecessary exposure to the patient.

Two dimensional sensor arrays placed on the opposite side of the patient from the beam generator 1 may be used to gather position feedback data. This approach provides adequate feedback to assure the exit mirrors 4b are creating the desired intersection point 9 inside the patient given the sensor array has adequate resolution.

Energy loss at each mirror should be on the order of 1 percent if the critical angle of 0.58 degrees is not exceeded. If a total of 6 mirrors are used along each path the total energy loss from the deflections should be approximately 6 percent. In addition, there may be an energy loss associated with the waveguides 5.

If there is no loss associated with entry into the waveguides 5, a beam processor with 101 ports would result in a peak photon density (number of photons per unit volume) within the intersection point 9 that is approximately 95 times greater than what is currently available from the same x-ray source without the beam processor at the distance from the source where the photons enter the beam processor. In actual practice, the patient would most likely be farther from the source. This would result in an even greater multiplier than 95.

Even if there is an energy loss of 20% associated with entry into the waveguides the beam processor according to the embodiment of the present invention would yield a peak concentration in the intersection point 9 that would be approximately 75 times greater than without the beam processor.

Sensor material is used around the entry to each port in the waveguide 5 to provide feedback information to aim the photons into the port.

Figure 4:
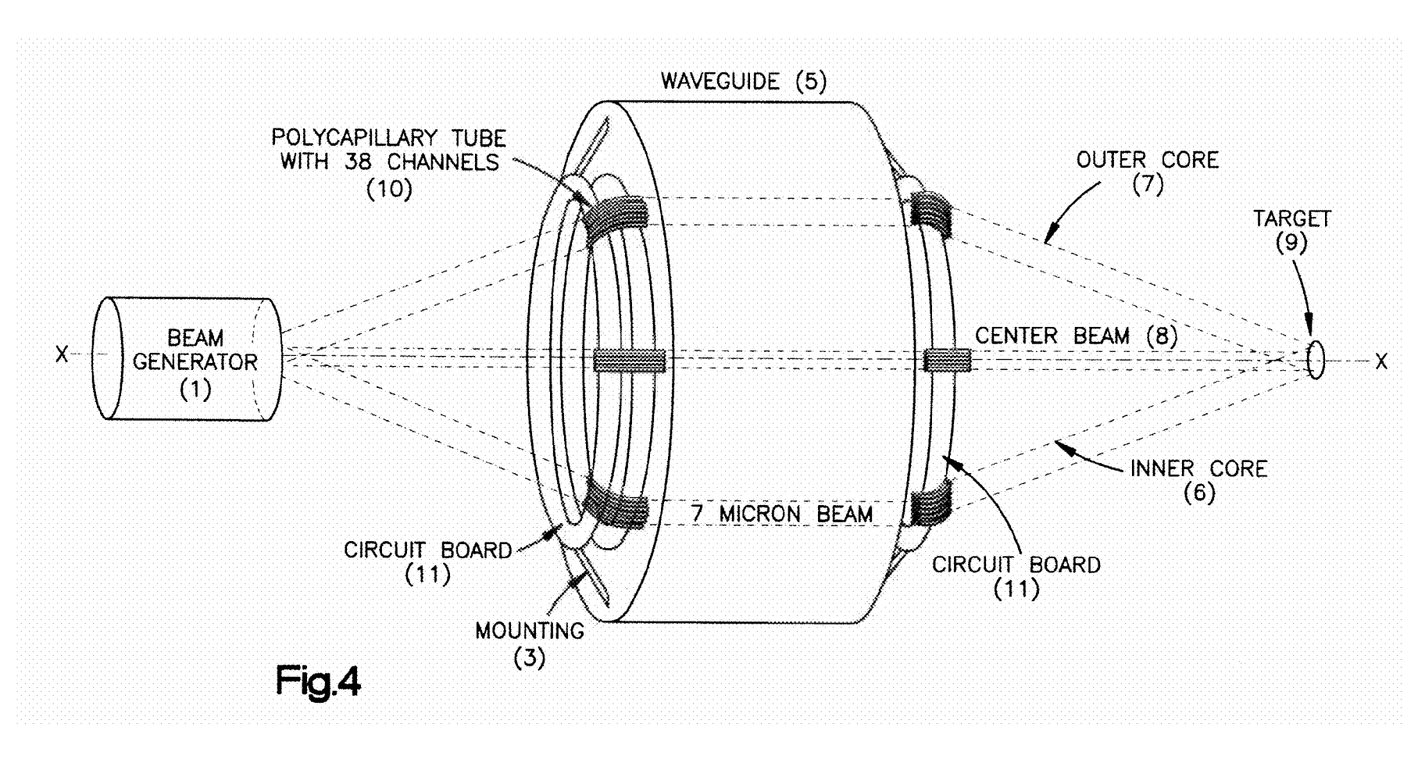
FIG. 4 is a side view of another embodiment of the present invention showing the components in an alternative optic system that includes polycapillary tubes.

FIG. 4 is a side view of another embodiment of the present invention showing the components in an alternative optic system that includes polycapillary tubes 10 with channels. In this embodiment, hundreds of polycapillary tubes 10 can be placed on chips 13 (not shown) on the circuit board 11. The number of polycapillary tubes 10 can be doubled by placing them on the inside and outside of the circuit board 11. Each polycapillary tube 10 can be actuated separately to change the direction of the beam. There are preferably 38 channels in each tube, with each channel in the tube being preferably 1 micron in diameter and each tube preferably having a 7 micron diameter.

In the beam processor shown in FIG. 4, actuated polycapillary tubes on chips 10 are used to direct elements of a diverging x-ray beam into preferably 513 gold-plated, seven micron, waveguide channels 12 which are approximately three feet in length in a lead cylinder. At the exit the beams are aimed at the target 9 with a ring of actuated polycapillary tubes on chips 10. The polycapillary tubes on chips 10 can be used to turn off certain waveguides 5 for alignment checks for each mirror individually and to reduce flux as needed.

X-ray beams from the beam generator 1 are preferably captured by a ring of over 500 polycapillary optic chips 13 and directed into waveguide 5 ports. The polycapillary optic chips 13 preferably contain 38 channels forming one 7 micron tube. Each optic chip is preferably actuated to turn each waveguide 5 "on" or "off" to control flux. The waveguide 5 is preferably cylindrical. Each waveguide 5 would preferably include a 7 micron, gold-plated tube in a cylindrical shaped lead shield approximately one meter in length. The beams would then exit the waveguide 5 and be directed to the target 9 by a ring of single or multiple actuated mirrors 4.

Figures 5A, 5B:
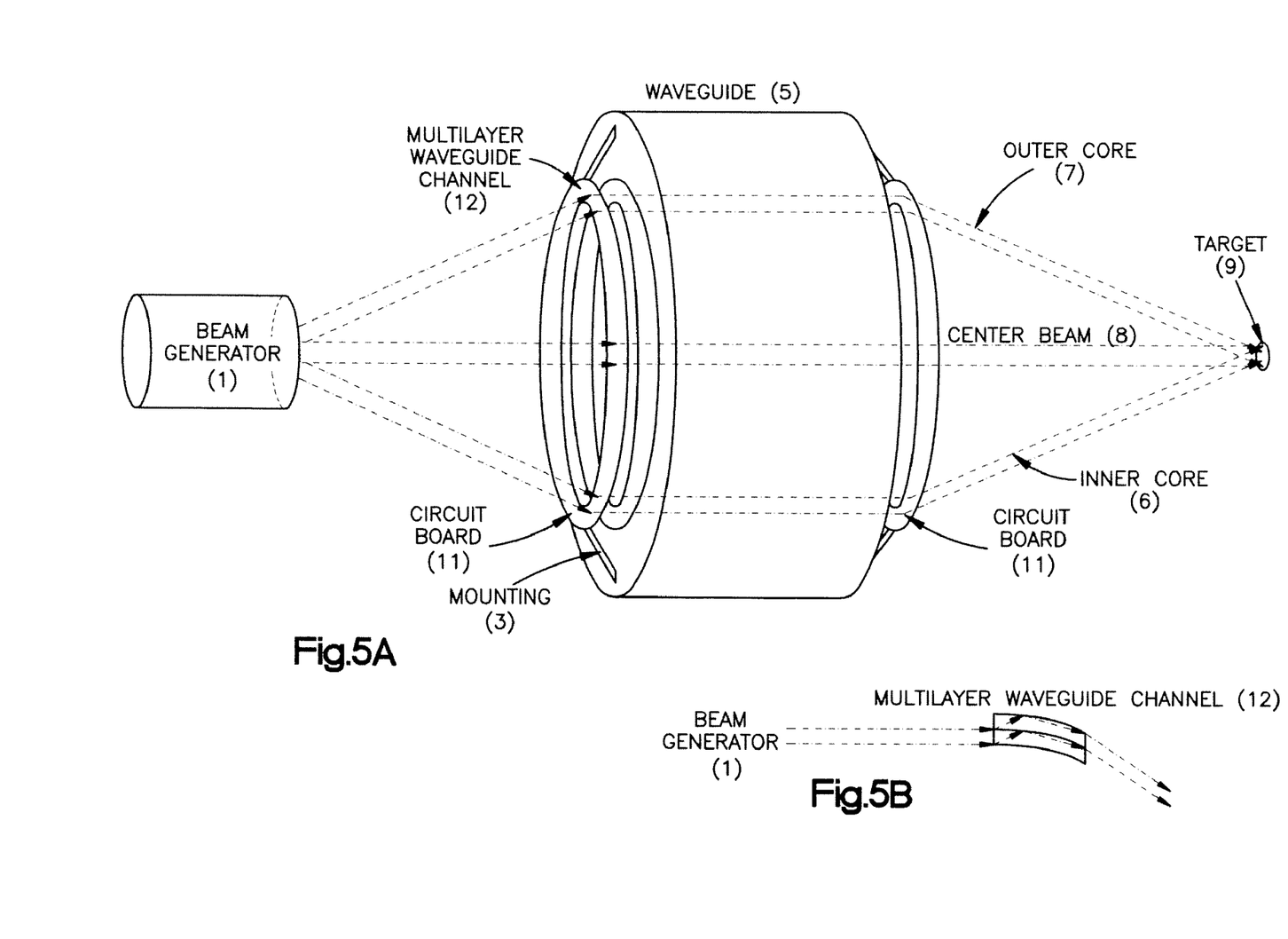
FIG. 5A is a side view of yet another embodiment of the present invention showing the components in an alternative optic system that includes multilayer waveguide channels.
FIG. 5B is a side view of an embodiment of the present invention showing the directional change that occurs when x ray beams come in contact with a multilayer waveguide channel.

FIG. 5A is a side view of yet another embodiment of the present invention showing the components in an alternative optic system that includes multilayer waveguide channels 12. FIG. 5B is a side view of an embodiment of the present invention showing the directional change that occurs when x ray beams come in contact with a multilayer waveguide channel 12. This embodiment is similar to the one described in FIG. 4 except that waveguide channels mounted on actuated chips are used to direct the x-ray beams into the waveguide channels.

Figure 6:
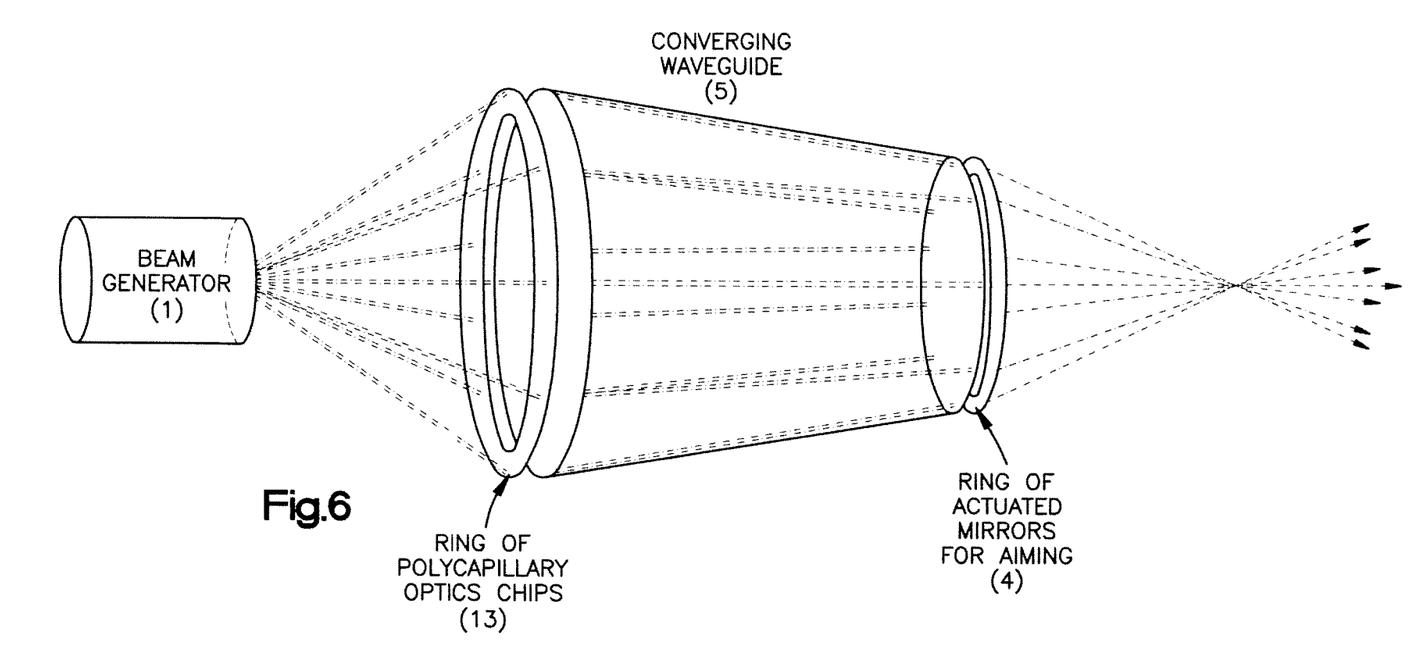
FIG. 6 is a view of another embodiment of the present invention showing the components in an alternative optic system that includes a beam processor with converging waveguides.

FIG. 6 is a side view of yet another embodiment of the present invention showing the components in an alternative optic system that includes a ring of polycapillary optic chips as described in FIG. 4 which guide the x-ray beams into a converging multilayer waveguide. The multi-layers are preferably alternating thin layers of dense and light materials. The x-rays are then aimed at the target 9 by a ring of actuated single or multiple mirrors 4b at the exit of the waveguide 5.

Figure 7:
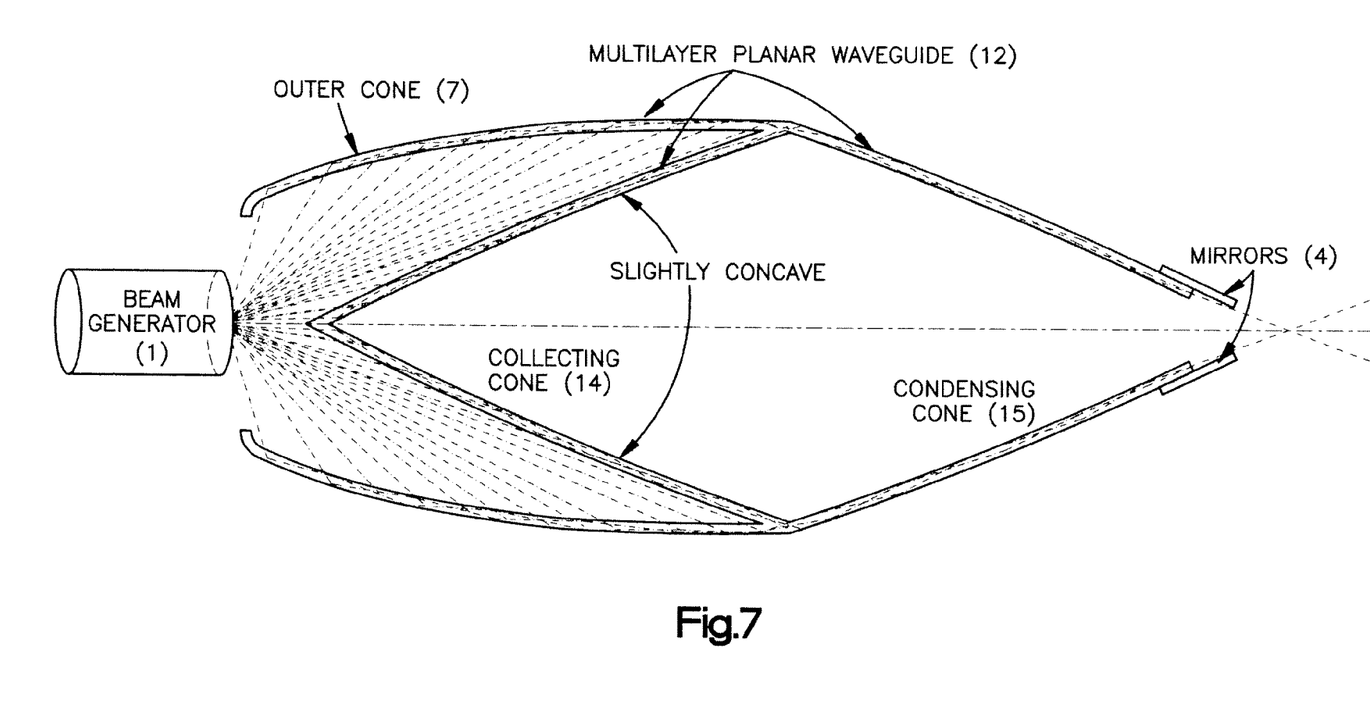
FIG. 7 is a side view of yet another embodiment of the present invention showing the components in an alternative optic system that includes double cone optics.

In the beam processor shown in FIG. 7, multi-layered planar waveguide optics are wrapped into a diverging cone on a preferably smooth stainless steel substrate. The multi-layers are preferably alternating thin layers of dense and light materials. In this embodiment, the x-ray beams are preferably coupled to the waveguide 5 by resonant beam coupling. The diverging cone will be the inner collecting cone. It will preferably be slightly concave with respect to incoming beams. X-ray beams are collected on the outer surface of the diverging cone.

In addition, an outer collecting cone which is preferably slightly convex with respect to the incoming beams will collect beams with a wider angle of divergence from the beam source. The outer cone 7 will also preferably be a multi-layered planar waveguide 5 which will be wrapped into a slightly diverging cone. This cone will collect x-ray beams on its inner surface.

As shown on FIG. 7, the outer and inner cones meet at the widest part of the cones forming one planar waveguide 5. As a person of ordinary skill in the art would readily understand, flux increases as the cones widen, collecting more and more x-ray beams of diverging angles. As shown in FIG. 6, the planar waveguide 5 then forms a converging cone, which is also referred to as a condensing cone, that includes straight angles. In the condensing cone, the x-rays increase in coherence and adherence. As the x-rays exit the waveguide 5 they are aimed at the target 9 by a ring of single or multiple actuated mirrors 4.

FIG. 7 is a side view of yet another embodiment of the present invention showing the components in an alternative optic system that includes double cone optics. As shown in FIG. 7, the collecting and condensing cones are continuous and are made as one unit by coating a preferably stainless steel substrate with alternating layers of dense and light materials. Alternatively, the collecting and condensing cones could be made separately and be linked in the middle by a ring of polycapillary optics. These polycapillary optics may be mounted on actuated chips 13 such that photons are directed into the condensing cone or kept out of the condensing cone to control flux. On the other hand, the collecting and condensing cones could be made separately and be linked in the middle by ring shaped multi-layered waveguides on actuated chips 13 to control flux. In addition, in this embodiment, it is preferred that cooling tubes be used in the core to cool the surface. In both of the above alternatives a lead shield is preferably placed after the actuated chips 13 on the outside of the cone to absorb x-rays when the optic chips 13 are turned to the "off" position. Each chip is preferably controlled separately for alignment and control.

Figure 8:
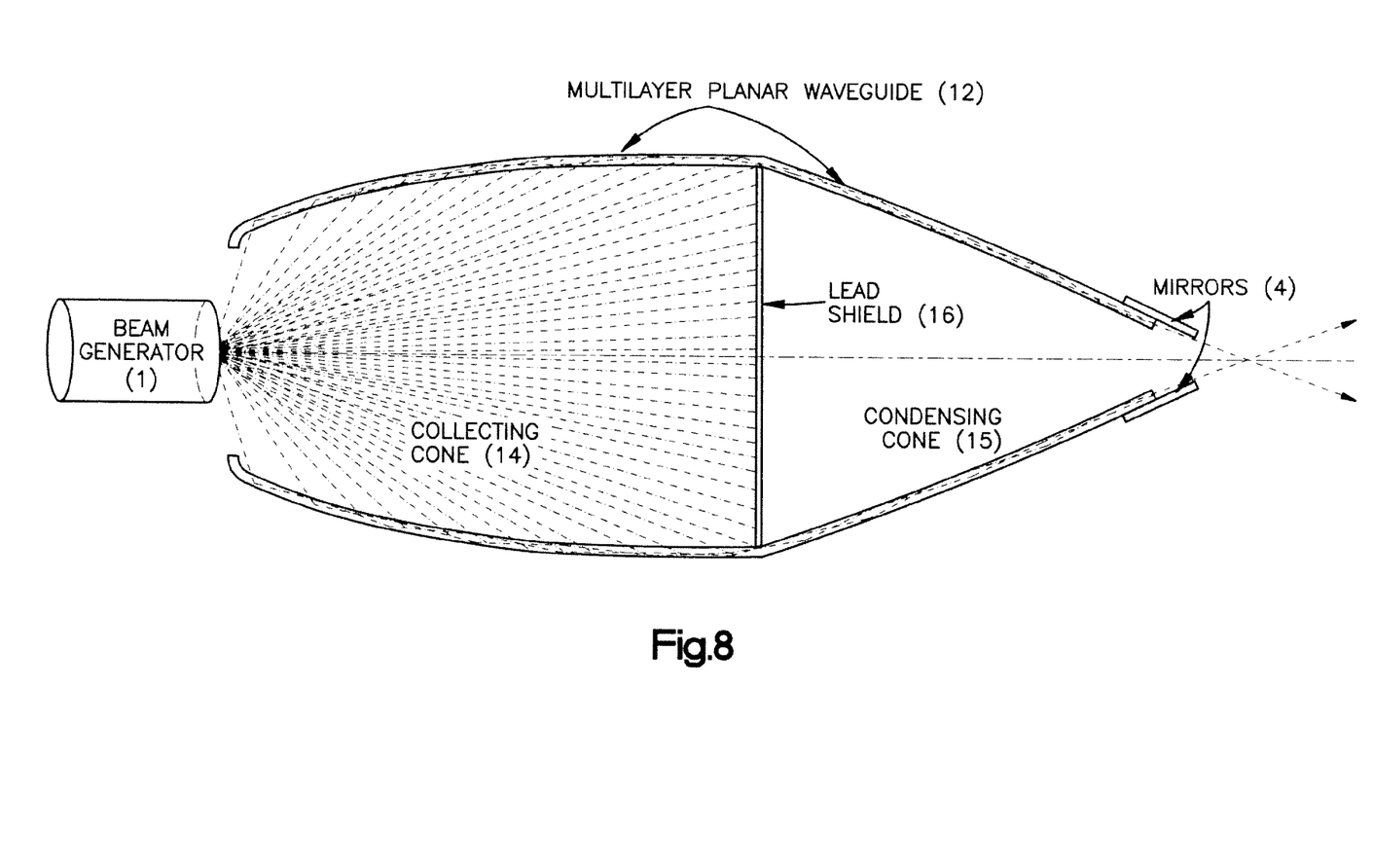
FIG. 8 is a side view of another embodiment of the present invention showing the components in an alternative optic system that includes inner cone optics.

FIG. 8 is a side view of another embodiment of the present invention showing the components in an alternative optic system that includes inner cone optics. Based on a comparison of FIGS. 7 and 8, the inner cone optics shown in FIG. 8 are similar to FIG. 7 related to multi-layered planar waveguide optics except that FIG. 8 shows an outer cone 7 used to collect x-ray beams on its inner surface. FIG. 8 shows a beam processor that is made of a multi-layer planar waveguide 5 wrapped into a diverging cone with slightly convex sides. This waveguide 5 is connected to a condensing cone 15 made of a multi-layer planar waveguide 5 wrapped into a converging cone with straight sides. As shown in FIG. 8, where the cones meet there is a lead shield in the center to prevent unchanneled x-ray beams from entering the condensing cone. The cones are preferably rigid and are preferably actuated as a unit for aiming. In this embodiment, lead leafs are used to form an aperture at the inlet of the collecting cone 14 which, as shown in FIG. 8, is preferably situated adjacent to the beam generator 1. Because the collecting cone 14 is immediately adjacent to the beam generator, all of the x-ray beams are inside the collecting cone 14 (hence, that is why this embodiment is referred to as the "inner cone optics"). When used in this manner, the collecting cone 14 will channel the more divergent beams.

Alternatively, as shown in FIG. 7, and described above, the diverging and converging cones can be linked by a ring of polycapillary tubes 10 or multi-layer waveguides on actuated chips 13 for controlling flux.

Alternatively, as shown in FIGS. 4 and 5, the exiting beams could be manipulated with a ring of single or multiple actuated mirrors 4 for aiming. In this embodiment, there may be two beams exiting each channel in different directions. This may require a lead shield to absorb unwanted x-ray beams at the center of the exit cone of the waveguide 5.

Figure 9:
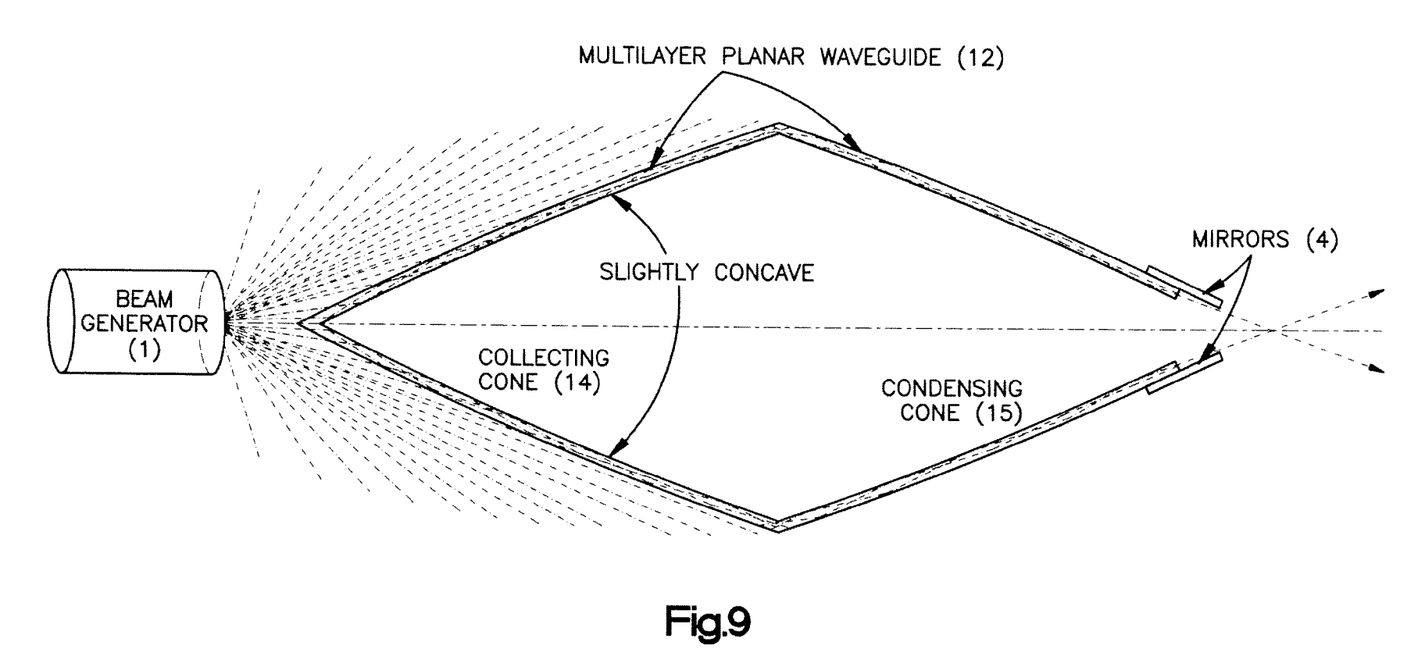
FIG. 9 is a side view of yet another embodiment of the present invention showing the components in an alternative optic system that includes outer cone optics.
Figure 10:
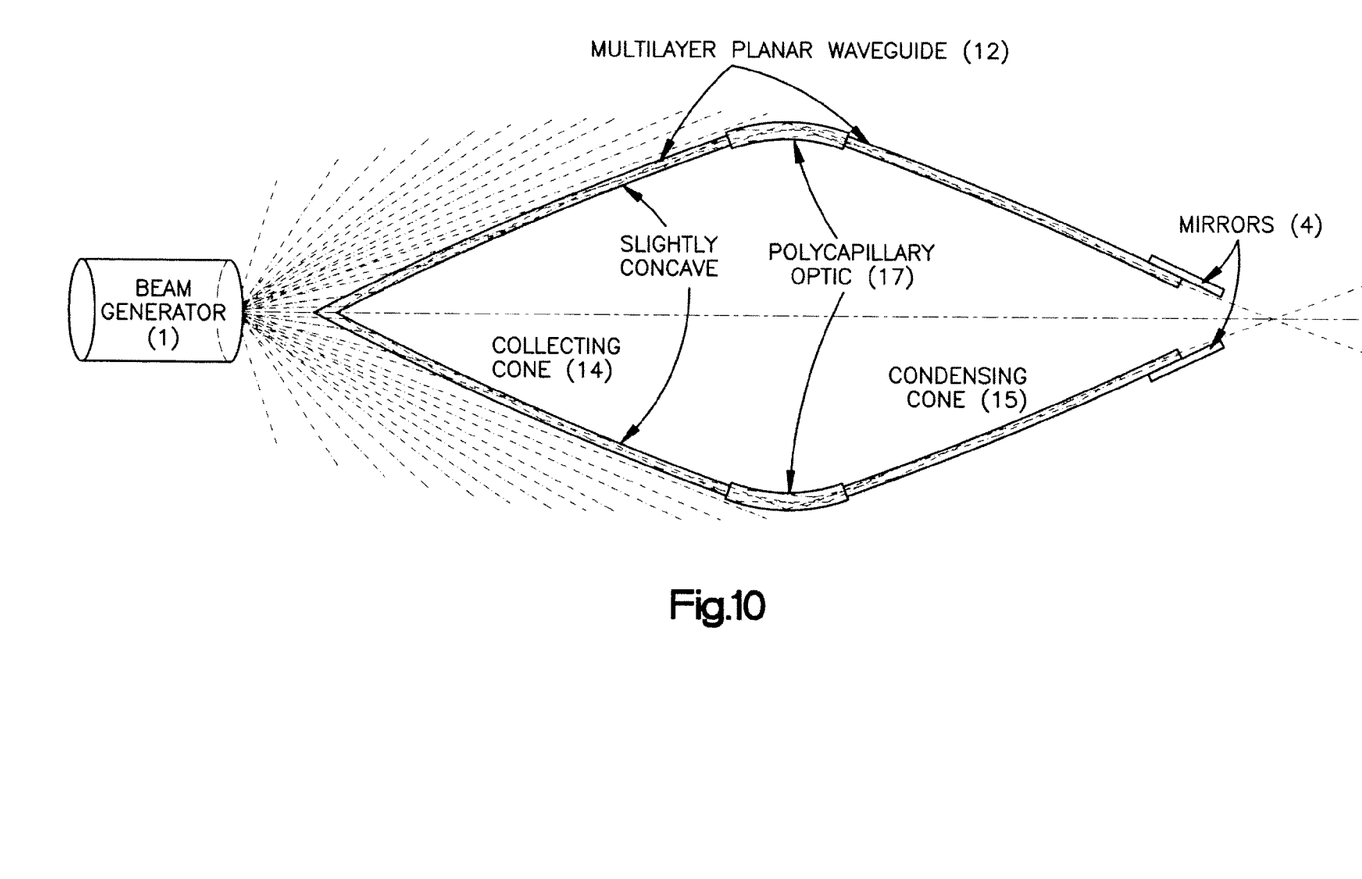
FIG. 10 is a side view of another embodiment of the present invention showing the components in an alternative optic system that includes outer cone optics with polycapillary tubes.

FIGS. 9 and 10 are side views of an embodiment of the present invention showing the components in an alternative optic system that includes outer cone optics, where FIG. 10 further includes outer cone optics with polycapillary tubes 10. The outer cone optics shown in FIGS. 9 and 10 are similar to the aspects shown in FIG. 7 and described above except that in FIG. 7, only the inner cone is used to collect x-ray beams. In contrast, FIGS. 9 and 10 show the x-rays being collected on the outside of the cone. It is made of a multi-layer planar waveguide 5 wrapped into a diverging cone with slightly concave sides. This waveguide is connected to a condensing cone 15 made of a multi-layer planar waveguide 5 wrapped into a converging cone. Beams are aimed by a ring of actuated exit mirrors 4b at the exit of the cone.

As shown in FIGS. 4 and 5, and described above, the diverging and converging cones can be linked by a ring of polycapillary tubes 10 or multi-layer waveguides on actuated chips 13 for controlling flux.

Various sections of the different beam processors may be put together to form different beam processors for various applications. For example, a person of ordinary skill in the art would readily understand that the collecting cone 14 could be used with the converging waveguide 5. In addition, polycapillary optics or multi-layer planar waveguides on actuated chips 13 could be used in the hinge area between the collecting cone 14 and the converging waveguide 5.

I claim:

1. An x-ray beam processor system comprising:
    x-ray beam generator for generating x-ray beams;
    a mirror shield member for shielding the x-ray beams from select areas;
    a cylindrical waveguide for guiding x-ray beams traveling through the waveguide, which includes a plurality of entry ports and exit ports;
    a plurality of ring-shaped mirrors disposed adjacent to and generally parallel with the entry ports and the exit ports, and sharing a common axis "X" with the waveguide; and
    a plurality of mountings for mounting the mirrors to the waveguide,
    wherein the mirrors are piezoelectric actuated to control their movement.

2. The beam processor system according to claim 1, wherein the beam generator includes linear accelerators, x-ray tubes or radioactive isotopes.

3. The beam processor system according to claim 1, wherein the mirrors include entry mirrors disposed on a beam generator side of the waveguide and exit mirrors disposed on a target side of the waveguide.

4. The beam processor system according to claim 3, wherein the exit mirrors direct x-ray beams from the exit ports to a target including cancer cells.

5. The beam processor system according to claim 1, wherein the mirror shield includes a lead material.

6. The beam processor system according to claim 1, wherein the entry ports and exit ports interior circumferences are gold plated.

7. The beam processor system according to claim 1, wherein the x-ray beams traveling from the beam generator through a center port and onto a target form a center beam.

8. The beam processor system according to claim 1, wherein a base of the mirror is fixed to the mounting while the mirror is actuated relative to the base.

9. The beam processor system according to claim 1, wherein the waveguide further includes an outer ring, an inner ring and a center port.

10. The beam processor system according to claim 9, wherein the x-ray beams traveling to the outer ring and the inner ring form inner and outer cones between the beam generator and the entry ports, and again form inner and outer cones as the x-ray beams travel from the exit ports to the target.

11. An x-ray beam processor system comprising:
    x-ray beam generator for generating x-ray beams;
    a mirror shield member for shielding the x-ray beams from select areas;
    a cylindrical waveguide for guiding x-ray beams traveling through the waveguide, which includes a plurality of entry ports and exit ports;
    a plurality of ring-shaped circuit boards disposed adjacent to and generally parallel with the entry ports and the exit ports, and sharing a common axis "X" with the waveguide, wherein the circuit boards include a plurality of electrical chips;
    a plurality of polycapillary tubes with channels connected to the electrical chips; and
    a plurality of mountings for mounting the circuit boards to the waveguide,
    wherein the polycapillary tubes are actuated to change a direction of the beam.

12. The x-ray beam processor system according to claim 11, wherein the polycapillary tubes can be actuated separately.

13. The x-ray beam processor system according to claim 12, wherein there are approximately 38 channels in each polycapillary tube, with each channel being approximately 1 micron in diameter and each polycapillary tube having a 7 micron diameter.

14. The x-ray beam processor system according to claim 11, further comprising an approximate 513 gold-plated, seven micron, waveguide channels which are approximately three feet in length in a lead cylinder.

* * * * *